United States Patent [19]
Wilk et al.

[11] Patent Number: 5,234,439
[45] Date of Patent: Aug. 10, 1993

[54] METHOD AND INSTRUMENT ASSEMBLY FOR REMOVING ORGAN

[76] Inventors: Peter J. Wilk, 185 West End Ave., New York, N.Y. 10023; Naomi L. Nakao, 303 E. 57th St., New York, N.Y. 10022

[21] Appl. No.: 926,762
[22] Filed: Aug. 6, 1992
[51] Int. Cl.⁵ .................. A61B 17/00; A61B 19/00
[52] U.S. Cl. .................................. 606/114; 606/1; 606/110; 606/113; 606/127
[58] Field of Search .............. 128/749, DIG. 24; 606/1, 110, 114, 113, 127, 39-52; 600/37

[56] References Cited

U.S. PATENT DOCUMENTS

| | | |
|---|---|---|
| 460,940 | 10/1891 | Baugh . |
| 1,609,014 | 11/1926 | Dowd . |
| 3,715,829 | 2/1973 | Hamilton . |
| 4,516,347 | 5/1985 | Dickie . |
| 4,557,255 | 12/1985 | Goodman . |
| 4,997,435 | 3/1991 | Demeter . |
| 5,037,379 | 8/1991 | Clayman et al. .......... 600/37 |
| 5,084,054 | 1/1992 | Bencini et al. . |
| 5,143,082 | 9/1992 | Kindberg et al. .......... 128/D24 |
| 5,147,371 | 9/1992 | Washington .......... 606/113 |
| 5,158,561 | 10/1992 | Rydell .......... 606/113 |

FOREIGN PATENT DOCUMENTS 606127 1/1884 Brazil .

Primary Examiner—Stephen C. Pellegrino
Assistant Examiner—Glenn Dawson
Attorney, Agent, or Firm—R. Neil Sudol; Henry D. Coleman

[57] ABSTRACT

A method for removing a gall bladder comprises the steps of (a) providing a surgical instrument including a flexible loop and a flexible web member connected to said loop to form a capture pocket, the loop defining a mouth opening of the pocket, (b) closing the cystic duct, (c) severing the cystic duct, and (d) passing the loop around a portion of the gall bladder including a closed and severed segment of the cystic duct, thereby enclosing the gall bladder portion in the capture pocket. The method further comprises the steps of (e) severing connective tissue between the gall bladder and the adjacent liver subsequently to the passing of the loop around the bladder, (f) maintaining the gall bladder portion surrounded by the capture pocket during the severing of the connective tissue, and (g) shifting the loop relative to the gall bladder to enclose a greater portion of the gall bladder in the capture pocket upon a severing of some of the connective tissue between the gall bladder and the adjacent liver. The method is adaptable to removing other internal organs, particularly organs which are coupled to adjacent tissue masses via connective tissue.

20 Claims, 3 Drawing Sheets

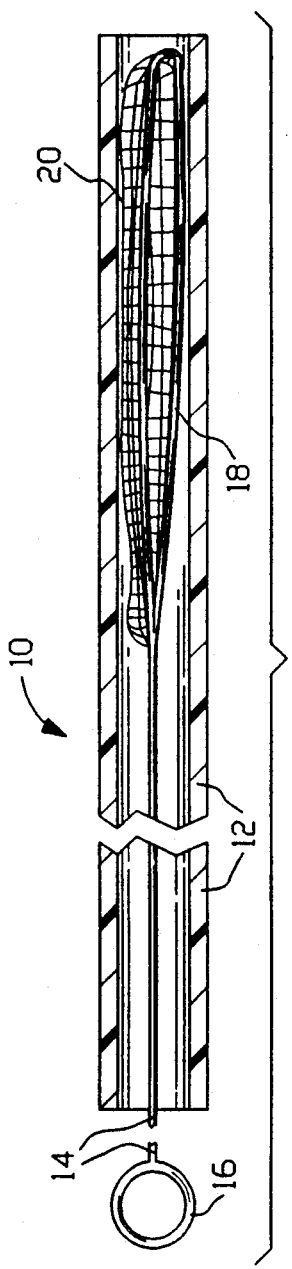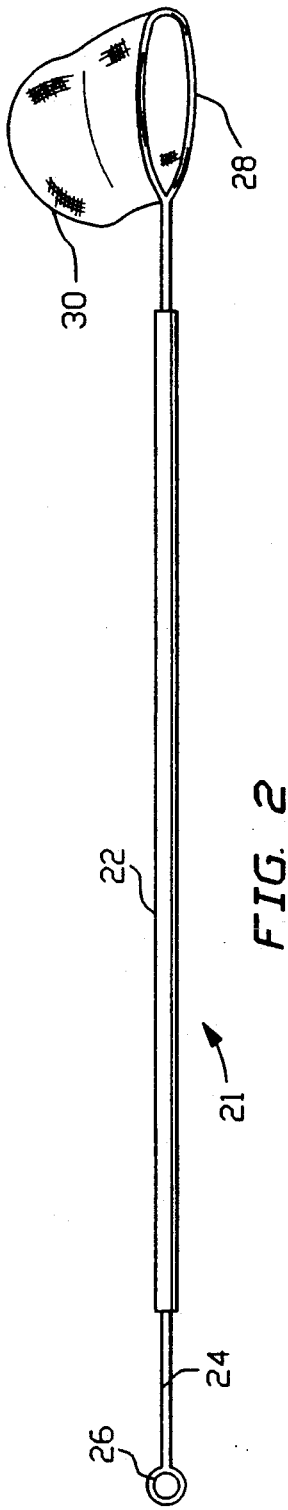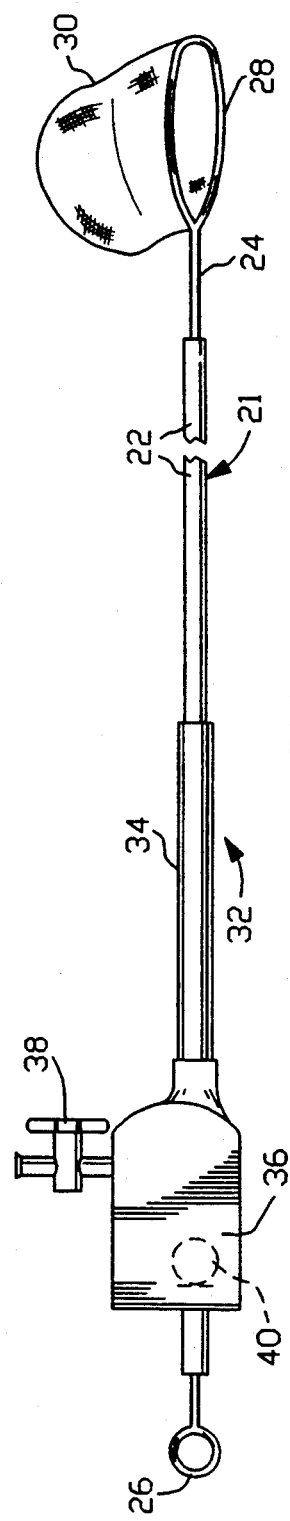

METHOD AND INSTRUMENT ASSEMBLY FOR REMOVING ORGAN

BACKGROUND OF THE INVENTION

This invention relates to a method for removing an internal organ of a patient. More particularly, this invention is directed to a method for removing such an organ which is coupled to adjacent tissues or organs via connective tissue The invention is particularly suitably for removing a gall bladder but may additionally be used for removing other organs or portions of organs. This invention also relates to an instrument assembly utilizable in the method.

A commonly performed surgical operation is the removal of gall bladders. When a bladder fills with stones, it must be removed.

Conventionally, gall bladders are removed through abdominal surgery. A long incision is made in the abdominal wall and the surgeon operates on the open abdominal organs. This procedure requires a substantial quantity of blood for transfusion to the patient. In addition, hospitalization time is long and recuperation is painful.

Other organs internal to a patient such as an ovary, a uterus, a bowel section or an appendix are conventionally removed through open abdominal surgery. The disadvantages of open abdominal surgery are common to all such procedures.

A new kind of surgery used in the removal of gall bladders is laparoscopic surgery.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity. The laparoscope is a fiber optic instrument which enables visualization of internal organs, for example, on a video monitor connected to the laparoscope.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle is inserted through the abdominal wall to enable pressurization of the abdominal cavity with carbon dioxide. This insufflation procedure distends the abdominal wall, thereby producing a safety space above the patient's abdominal organs.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

In removing a gall bladder through laparoscopic surgery, one instrument is generally a forceps. The forceps is manipulated from outside the patient to grasp the gall bladder and to pull it away from the liver during a severing of connective tissue by another laparoscopic instrument which is inserted into the abdominal cavity through another trocar sleeve.

Sometimes the gall bladder is thin and perforates upon being grasped by the forceps. In that case, bile in the bladder spills out into the abdomen. In addition, one or more gall stones are occasionally lost. Such an eventuality is not conducive to patient care and warrants a time consuming search for the lost stone or stones.

OBJECTS OF THE INVENTION

An object of the present invention is to provide a method for use in the surgical removal of an organ internal to a patient.

A more particular object of the present invention is to provide such a method for removing a gall bladder.

Another, even more particular, object of the present invention is to provide a laparoscopic technique for use in the surgical removal of a gall bladder.

An additional particular object of the present invention is to provide such a method or technique which reduces the chances of bladder rupture or perforation during an operation.

A further particular object of the present invention is to provide such a method or technique which facilitates the removal of the severed gall bladder from the abdomen.

Yet another particular object of the present invention is to provide an associated instrument assembly for use in such a method or technique.

Other objects of the present invention will be apparent from the detailed descriptions and drawings included herein.

SUMMARY OF THE INVENTION

The present invention is directed to a method for removing an organ internal to a patient, the organ being coupled to internal tissues via at least a mass of connective tissue. The method comprises the steps of (a) providing a surgical instrument including a flexible loop and a flexible web member connected to the loop to form a capture pocket, the loop defining a mouth opening of the pocket, (b) passing the loop around a portion of the organ, thereby enclosing the organ portion in the capture pocket, (c) severing connective tissue between the organ and adjacent tissues subsequently to the passing of the loop around the organ portion, (d) maintaining the organ portion surrounded by the capture pocket during the severing of connective tissue, and (e) shifting the loop relative to the organ to enclose a greater portion of the organ in the capture pocket upon a severing of some of the connective tissue between the organ and the adjacent tissues.

Where the organ to be removed communicates with adjacent organs via at least one duct-like connection, the method further comprises the steps of closing the duct-like connection and severing the duct-like connection. In some cases, for example, where the organ to be removed is a gall bladder connected to adjacent tissues via a cystic duct, the closing and severing of the duct are performed prior to passage of the loop around the organ. It is also preferred that the loop is passed around a portion of the gall bladder which includes a closed and severed segment of the cystic duct, thereby enclosing the bladder portion in the capture pocket.

The instant technique may be used to remove organs other than the gall bladder, for example, an ovary, an appendix, a uterus, or a section of bowel.

Pursuant to another feature of the present invention, the method also comprises the step of constricting the loop about the subject organ after the completed passing of the loop about the organ. The constricting of the loop serves to grasp the organ in the loop. This constriction of the loop facilitates another step in the procedure, which is to exert force on the loop to pull the organ away from the adjacent tissues during the severing of the connective tissues. However, it is not necessary to constrict the loop in all cases. A relatively loose loop may still function to pull the organ away from the adjacent tissues, particularly in more advanced stages of the procedure, where a greater portion of the organ is firmly ensconced within the capture pocket.

Near the end of the operation, the loop is moved relative to the organ to surround the entire organ. This step can occur only upon a severing of all connective tissue between the organ and the adjacent tissues. The enclosure of the organ in the capture pocket facilitates withdrawal or extraction of the severed organ from the patient.

According to another feature of the present invention, the loop is connected to a distal end of an elongate slider member which is slidably inserted through an elongate tubular member. The constriction of the loop is then accomplished by pulling the elongate slider member in a proximal direction through the tubular member, thereby drawing at least a portion of the loop into a distal end of the tubular member.

Preferably, the method in accordance with the present invention is a laparoscopic technique. Accordingly, the steps of closing, severing, passing, and shifting are all implemented through trocar sleeves extending through the abdominal wall of the patient.

To wit, a method for removing a gall bladder comprises, in accordance with the present invention, the steps of (i) piercing an abdominal wall of a patient to form a pair of openings in the abdominal wall, (ii) disposing a first tubular cannula in one of the openings, (iii) disposing a second tubular cannula in another of the openings, (iv) providing a first surgical instrument including a flexible loop and a flexible web member connected to the loop to form a capture pocket, the loop defining a mouth of the pocket, (v) inserting the loop and the web member through the first tubular cannula into the abdomen of the patient, (vi) inserting a second surgical instrument through the second tubular cannula into the abdomen of the patient, (vii) passing the loop around a portion of a gall bladder including a closed and severed cystic duct segment, thereby enclosing the gall bladder portion in the capture pocket, (viii) using the second surgical instrument to sever connective tissue between the gall bladder and the adjacent liver subsequent to the passing of the loop around the bladder, (ix) maintaining the gall bladder portion surrounded by the capture pocket during the step of using the second surgical instrument, and (x) shifting the loop relative to the gall bladder to enclose a greater portion of the gall bladder in the capture pocket upon a severing of some of the connective tissue between the gall bladder and the adjacent liver.

A surgical instrument assembly for use in retrieving objects such as organs from internal body cavities comprises, in accordance with the present invention, a rigid trocar sleeve provided at a proximal end with an insufflation stopper, an elongate tubular member inserted through the trocar sleeve and the insufflation stopper, and an elongate slider member slidably inserted through the tubular member. The slider member is longer than the tubular member and is provided at a distal end with a flexible loop. A flexible web member is connected to the loop to form a capture pocket, the loop defining a mouth of the pocket.

The instrument assembly may further comprise a manually actuatable shifter operatively connected to the slider member for longitudinally sliding the slider member along the tubular member in alternately opposite directions.

Pursuant to another feature of the present invention, the flexible web member is a net or a continuous film of polymeric material. The web is preferably stored in a collapsed configuration together with the loop inside the tubular member at a distal end thereof prior to the surgical procedure.

A method in accordance with the present invention for use in the surgical removal of a gall bladder reduces the chances of bladder rupture or perforation during an operation. The force exerted on the gall bladder is distributed in a circular locus about the bladder, rather than being concentrated at one point, for example, the jaws of a forceps attached to the bladder.

The automatic enclosure of the bladder in the capture pocket by the end of the procedure facilitates the removal of the severed gall bladder from the abdomen.

BRIEF DESCRIPTION OF THE DRAWING

FIG. 1 is a schematic longitudinal cross-sectional view of a surgical instrument on an enlarged scale for use in a method in accordance with the present invention, showing a capture net in a retracted storage configuration.

FIG. 2 is a schematic side elevational view, on a substantially reduced scale, of another surgical instrument for use in a method in accordance with the present invention, showing a capture net in an extended use configuration.

FIG. 3 is a schematic side elevational view, on a substantially reduced scale, of a laparoscopic surgical instrument assembly in accordance with the present invention, showing a capture net and a troacar sleeve.

DETAILED DESCRIPTION

Figure 5B:
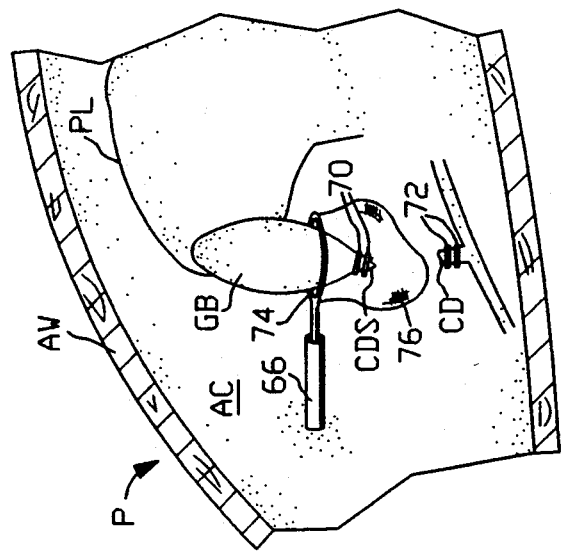
FIGS. 5A-5E are diagrams illustrating successive steps in a laparoscopic procedure in accordance with the present invention.

As illustrated in FIG. 1, a surgical instrument 10 for use in removing a gall bladder comprises a tubular member 12 and an elongate rod 14 slidably inserted in the tubular member. At a proximal end, rod 14 is provided with a finger ring 16 for facilitating a sliding of the rod through tubular member 12. At a distal end, rod 14 is provided with a flexible loop 18 to which a flexible web 20 in the form of a net is attached to form a capture pocket.

FIG. 1 shows loop 18 and net 20 in a collapsed configuration inside the distal end of tubular member 12. Upon a sliding of rod 14 in the distal direction, loop 18 and net 20 are ejected from the distal end of tubular member 12. Loop 18 naturally expands from the collapsed configuration to an expanded oval configuration. Net 20 also expands but to a much more limited extent. Generally, the expansion of net 20 is dependent on the expansion of loop 18 and the insertion of a gall bladder into the net, as described in detail hereinafter with reference to FIGS. 5A-5E.

As depicted in FIG. 2, another surgical instrument 21 for use in removing a gall bladder also comprises a tubular member 22 and an elongate rod 24 slidably inserted in the tubular member. Rod 24 is likewise provided with an actuator ring 26 at a proximal end and a flexible loop 28 at a distal end. A flexible web 30 in the form of a polymeric film is attached to loop 28 to form a capture pocket. FIG. 2 shows loop 28 and net 30 in an expanded configuration after a sliding of rod 24 in the distal direction through tubular member 22.

Surgical instruments 10 and 21 of FIGS. 1 and 2 may be used in conjunction with a laparoscopic cannula or trocar sleeve 32, as illustrated in FIG. 3 and as described in further detail hereinafter with reference to FIGS. 5A-5E. Trocar sleeve 32 and surgical instrument 21 together form a novel laparoscopic instrument assembly for use in removing a gall bladder.

As illustrated in FIG. 3, trocar sleeve 32 includes a rigid tubular member 34 and a port component 36 attached to a proximal end of the rigid tubular member. Port component 36 includes an insufflation valve 38 and an insufflation stopper 40. Tubular member 22 of surgical instrument 21 is inserted through tubular member 34 and insufflation stopper 40.

Figure 4:
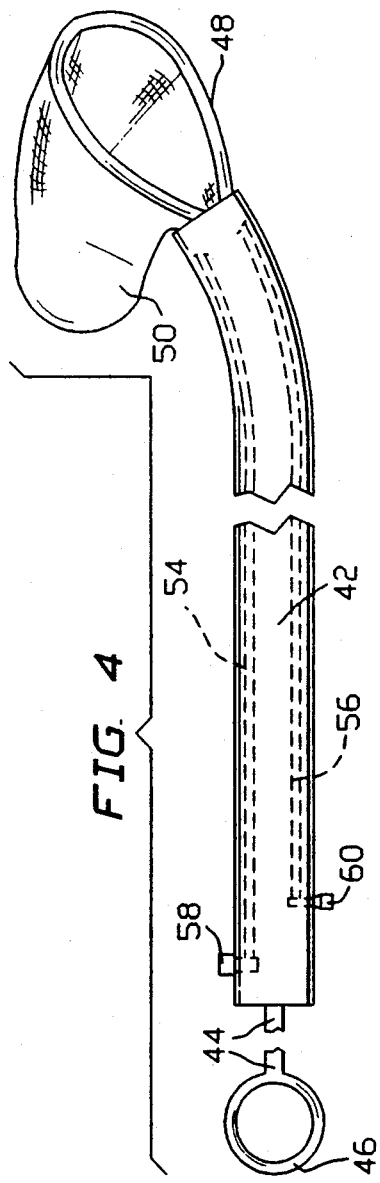
FIG. 4 is a schematic side elevational view, on an enlarged scale, of another surgical instrument for use in a method in accordance with the present invention.

As shown in FIG. 4, another surgical instrument 41 for use in a surgical procedure as described herein comprises a tubular member 42, an elongate slider rod 44 slidably inserted in tubular member 42, a finger ring 16 at the proximal end of rod 44, and a flexible, alternately expandable and contractible loop 48 at the distal end of rod 44. A net or web 50 is attached about loop 48 to form a capture pocket. Tubular member 42 is provided along opposite sides with a pair of tensile elements or wires 54 and 56. At a proximal end, wires 54 and 56 are connected to slidable actuators 58 and 60, while at the distal end, wires 54 and 56 are secured to tubular member 42. Upon a differential application of force to actuators 58 and 60, the orientation of the distal end of tubular member 42 is adjusted to facilitate the positioning of loop 48 and web or net 50.

A laparoscopic surgical procedure for removing a gall bladder will now be described with reference to FIGS. 5A-5E. An abdominal wall AW of a patient P is pierced to form a pair of openings O1 and O2 in the abdominal wall. Respective tubular cannulas or trocar sleeves 62 and 64 are disposed in the openings. A laparoscopic surgical instrument 66 of a form described hereinabove with reference to one of FIGS. 1, 2, and 4 is inserted through sleeve 62 so that the instrument traverses abdominal wall AW. Another elongate laparoscopic surgical instrument 68 for cutting and cauterizing connective tissue is inserted through sleeve 64.

Prior to the insertion of instrument 66 through sleeve 62, the cystic duct CD of patient P is closed by two pairs of clips 70 and 72 and severed therebetween, as more clearly seen in FIG. 5B. Upon the insertion of the distal end of instrument 66 into the abdominal cavity AC of patient P, a flexible loop 74 is ejected from a distal end of the instrument, as described hereinabove with reference to FIGS. 1 and 2.

As illustrated in FIG. 5B, loop 74 is passed around a portion of the patient's gall bladder GB including a closed and severed cystic duct segment CDS. Then, a capture pocket 76 on loop 74 encloses or surrounds the gall bladder portion.

Figure 5A:
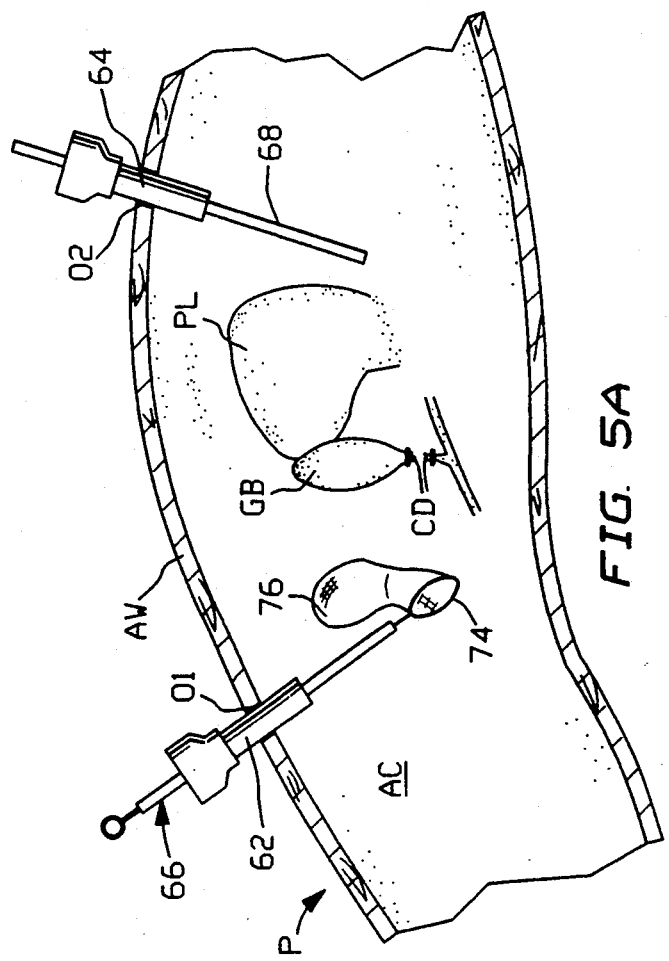
Figure 5C:
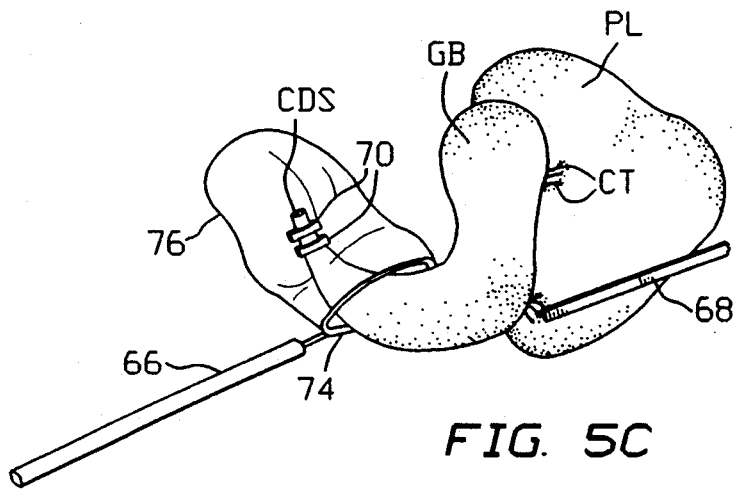

Subsequent to the passing of loop 74 around bladder GB, a surgeon uses surgical instrument 68 to sever connective tissue CT between gall bladder BG and the patient's liver PL, as depicted in FIG. 5C. During that operation, the free end portion of gall bladder GB is maintained inside capture pocket or web 76.

Figure 5D:
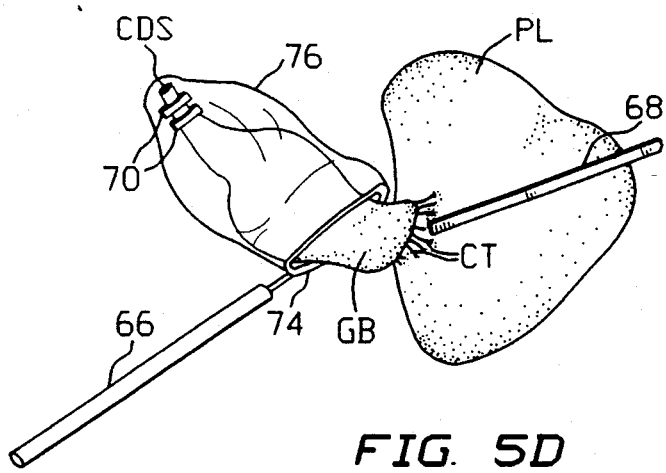
Figure 5E:
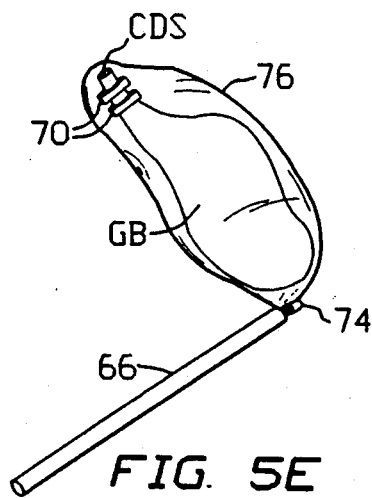

Upon a severing of sufficient amounts of connective tissue CT, loop 74 is shifted relative to gall bladder GB to enclose a greater portion of that organ in capture pocket 78, as depicted in FIG. 5D. Accordingly, it is to be understood that the sliding of loop 74 about gall bladder GB gradually encloses a greater and greater portion of bladder GB in pocker 76. As illustrated in FIG. 5E, bladder GB is eventually captured entirely in pocket 76 and is ready for removal from patient P.

It is to be noted that loop 74 is pulled away from liver PL during the severing of connective tissue CT by instrument 68, thereby facilitating the severing procedure. To ensure that the free end portion of bladder GB remains within web or pocket 76 during the pulling on loop 74, loop 74 may be tightened around the bladder. This tightening or constricting is effectuated by withdrawing or retracting loop 74 into the distal end of the instrument 66.

As indicated in FIG. 5E, capture pocket or bag 76 is be closed about gall bladder GB at the termination of the operation, i.e., upon severing of all connective tissue CT between bladder GB and liver PL. Such closure of loop 74 prevents an inadvertant escape of gall bladder GB from pocket 76.

The above-described technique may be used to remove organs other than the gall bladder, for example, an ovary, an appendix, a uterus, or a section of bowel. In each such case, the subject organ is coupled to internal tissues via some sort of connective tissue. The connective tissue may be the same kind of tissue, for instance, bowel wall in the case of a bowel section. The method essentially comprises the steps of passing a loop around a portion of the organ, thereby enclosing the organ portion in the capture pocket, and severing connective tissue between the organ and adjacent tissues subsequently to the passing of the loop around the organ portion, while maintaining the organ portion surrounded by the capture pocket. Subsequently, the loop is shifted relative to the organ to enclose a greater portion of the organ in the capture pocket upon a severing of some of the connective tissue between the organ and the adjacent tissues. Sooner or later, the entire organ is enveloped in the capture pocket and may be removed from the patient.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that the instrumentation and procedures described herein may be used in conventional open-incision surgery. In that event, tubular members 12, 22, etc. are not inserted through laparoscopic cannulas or trocar sleeves, as described above with reference to FIGS. 3 and 5A-5E. Instead, the instruments are guided through an open incision into the patient's abdomen. In view of the benefits of laparoscopic surgery and the increasing abandonment of conventional surgery in favor of that technique, it is contemplated that the greatest use of the present invention will be in laparoscopic surgery.

Accordingly, it is to be understood that the drawings and descriptions herein are proffered by way of example to facilitate comprehension of the invention and should not be construed to limit the scope thereof.

What is claimed is:

1. A method for removing an organ internal to a patient, said organ being coupled to internal tissues via at least a mass of connective tissue, the method comprising the steps of:
providing a surgical instrument including a flexible loop and a flexible web member connected to said loop to form a capture pocket, said loop defining a mouth opening of said pocket;
passing said loop around a portion of the organ, thereby enclosing the organ portion in said capture pocket;
subsequent to said step of passing, severing connective tissue between the organ and adjacent tissues;
maintaining said organ portion surrounded by said capture pocket during said step of severing connective tissue; and
upon a severing of some of the connective tissue between the organ and the adjacent tissues, shifting said loop relative to the organ to enclose a greater portion of the organ in said capture pocket.

2. The method defined in claim 1 wherein the organ to be removed is operatively coupled to adjacent organs via at least one duct-like connection, further comprising the steps of closing the duct-like connection and severing the duct-like connection.

3. The method defined in claim 2 wherein said steps of closing and severing the duct-like connection are performed prior to said step of passing, said organ portion including a closed and severed segment of the duct-like connection.

4. The method defined in claim 2 wherein said organ is a gall bladder and said duct-like connection is a cystic duct.

5. The method defined in claim 1, further comprising the step of constricting said loop about the organ after completion of said step of passing, thereby grasping the organ in the constricted loop.

6. The method defined in claim 5, further comprising the step of exerting force on said loop to pull the organ away from the adjacent tissues during said step of severing connective tissue.

7. The method defined in claim 5 wherein said loop is connected to a distal end of an elongate slider member slidably inserted through an elongate tubular member, said step of constricting comprising a step of pulling said elongate slider member in a proximal direction through said tubular member, thereby drawing at least a portion of said loop into a distal end of said tubular member.

8. The method defined in claim 1, further comprising the step of exerting force on said loop to pull the organ away from the adjacent tissues during said step of severing connective tissue.

9. The method defined in claim 1, further comprising the step of moving said loop relative to the organ to surround the entire organ upon a severing of all connective tissue between the organ and the adjacent tissues.

10. The method defined in claim 1 wherein the method is a laparoscopic technique, said steps of closing, severing, passing, and shifting being implemented through trocar sleeves extending through the abdominal wall.

11. The method defined in claim 1 wherein said web member is a net.

12. The method defined in claim 1 wherein the organ to be removed is an ovary.

13. The method defined in claim 1 wherein the organ to be removed is an appendix.

14. The method defined in claim 1 wherein the organ to be removed is a uterus.

15. The method defined in claim 1 wherein the organ to be removed is a section of bowel.

16. A method for removing a gall bladder, comprising the steps of:
piercing an abdominal wall of a patient to form a pair of openings in said abdominal wall;
disposing a first tubular cannula in one of said openings;
disposing a second tubular cannula in another of said openings;
providing a first surgical instrument including a flexible loop and a flexible web member connected to said loop to form a capture pocket, said loop defining a mouth of said pocket;
inserting said loop and said web member through said first tubular cannula into the abdomen of the patient;
inserting a second surgical instrument through said second tubular cannula into the abdomen of the patient;
passing said loop around a portion of a gall bladder including a closed and severed cystic duct segment, thereby enclosing the gall bladder portion in said capture pocket;
subsequent to said step of passing, using said second surgical instrument to sever connective tissue between the gall bladder and the adjacent liver;
maintaining said gall bladder portion surrounded by said capture pocket during said step of using said second surgical instrument; and
upon a severing of some of the connective tissue between the gall bladder and the adjacent liver, shifting said loop relative to the gall bladder to enclose a greater portion of the gall bladder in said capture pocket.

17. The method defined in claim 16, further comprising the step of constricting said loop about the gall bladder after completion of said step of passing, thereby grasping the gall bladder in the constricted loop.

18. The method defined in claim 17, further comprising the step of exerting force on said loop to pull the gall bladder away from the liver during said step of severing connective tissue.

19. The method defined in claim 17 wherein said loop is connected to a distal end of an elongate slider member slidably inserted through an elongate tubular member, said step of constricting comprising the step of pulling said elongate slider member in a proximal direction through said tubular member, thereby drawing at least a portion of said loop into a distal end of said tubular member.

20. The method defined in claim 16, further comprising the step of moving said loop relative to the gall bladder to surround the entire gall bladder upon a severing of all connective tissue between the gall bladder and the liver.

* * * * *